(12) United States Patent
Want et al.

(10) Patent No.: US 7,232,105 B2
(45) Date of Patent: Jun. 19, 2007

(54) METHOD AND APPARATUS FOR HANGING A MEDICAL DEVICE

(75) Inventors: Nicholas Want, Manchester, NH (US); Scott Edward Corbeil, Litchfield, NH (US); Marc A. Larochelle, Manchester, NH (US)

(73) Assignee: Atrium Medical Corporation, Hudson, NH (US)

( * ) Notice: Subject to any disclaimer, the term of this patent is extended or adjusted under 35 U.S.C. 154(b) by 150 days.

(21) Appl. No.: 10/694,147

(22) Filed: Oct. 27, 2003

(65) Prior Publication Data

US 2005/0087660 A1  Apr. 28, 2005

(51) Int. Cl.
*F16M 11/00* (2006.01)

(52) U.S. Cl. .................. 248/691; 248/215; 248/304; 248/308; 248/340; 248/341; 248/692; 128/DIG. 24; 604/322

(58) Field of Classification Search .............. 248/95, 248/215, 690–692, 339–341, 517, 304, 308; 215/399; 206/806; 220/751, 756, 759, 770; 128/DIG. 24; 604/322; 294/142, 143
See application file for complete search history.

(56) References Cited

U.S. PATENT DOCUMENTS

| 617,284 | A | * | 1/1899 | Darnes | 221/283 |
|---|---|---|---|---|---|
| 3,163,338 | A | * | 12/1964 | Gottsegen | 224/484 |
| 3,424,422 | A | * | 1/1969 | Klangos | 248/561 |
| 3,630,251 | A | * | 12/1971 | Ross | 220/751 |
| 3,690,315 | A | * | 9/1972 | Chittenden et al. | 604/324 |
| 3,804,310 | A | * | 4/1974 | Wheeler | 294/142 |
| 3,995,803 | A | * | 12/1976 | Uitz | 224/432 |
| 4,189,789 | A | * | 2/1980 | Hofstetter | 4/144.1 |
| 4,219,177 | A | * | 8/1980 | O'Day | 248/215 |
| 4,258,893 | A | * | 3/1981 | Tolley | 248/447.1 |
| 4,440,371 | A | * | 4/1984 | Wijsman | 248/318 |
| 4,658,834 | A | * | 4/1987 | Blankenship et al. | 600/584 |
| 4,747,843 | A | * | 5/1988 | Felix et al. | 604/318 |
| 4,750,697 | A | * | 6/1988 | Tontarelli | 248/215 |
| 4,756,501 | A | * | 7/1988 | Quercia et al. | 248/340 |
| 4,951,484 | A | * | 8/1990 | Rohald et al. | 70/59 |
| 5,224,607 | A | * | 7/1993 | Koresko | 211/34 |
| 5,352,006 | A | * | 10/1994 | Ocuin | 294/142 |
| 5,393,113 | A | * | 2/1995 | Walsh | 294/170 |
| 5,527,007 | A | * | 6/1996 | Weilbacher | 248/304 |
| 5,575,446 | A | * | 11/1996 | Swenson et al. | 248/304 |
| D393,587 | S | | 4/1998 | Valerio et al. | |
| 5,749,497 | A | * | 5/1998 | Davis | 222/181.2 |
| 5,865,408 | A | * | 2/1999 | Swisher et al. | 248/188.1 |
| D436,838 | S | * | 1/2001 | Kirk | D8/370 |
| 6,368,311 | B1 | | 4/2002 | Valerio et al. | |
| 6,651,941 | B1 | * | 11/2003 | Kinsel | 248/100 |

FOREIGN PATENT DOCUMENTS

JP  2000262590 A  *  9/2000

* cited by examiner

*Primary Examiner*—Korie Chan
(74) *Attorney, Agent, or Firm*—RatnerPrestia

(57) ABSTRACT

An apparatus for hanging a medical device is provided. The apparatus includes a shaft, a mounting portion coupled to an end portion of the shaft and configured for mounting the apparatus for movement with respect to the medical device, and a hook portion positioned at an opposite end portion of the shaft and configured for hanging the apparatus from a support. The shaft is configured to permit rotation of the hook portion with respect to the mounting portion, thereby facilitating orientation of the hook portion with respect to the support.

19 Claims, 4 Drawing Sheets

METHOD AND APPARATUS FOR HANGING A MEDICAL DEVICE

FIELD OF THE INVENTION

The present invention relates to an apparatus for hanging a medical device. More specifically, the present invention relates to an apparatus configured for hanging a medical device such as a chest drain to a support during use.

BACKGROUND OF THE INVENTION

A wide variety of medical devices are utilized in health care and hospital settings. One example of a medical device is a fluid recovery system such as a chest drain, also known as a thoracic cavity drain. Generally, a chest drain is a relatively compact bedside vessel employed to collect fluids postoperatively from a closed surgical site, for example, through a catheter implanted in the patient's chest.

A chest drain is sometimes positioned on a hospital room floor when it is difficult to find an appropriate support to which the chest drain can be mounted, which increases the difficulty of monitoring the volume of fluid collected within the collection chamber of the chest drain system or otherwise manipulating the chest drain.

Accordingly, there is a need for an apparatus that quickly and easily secures a medical device such as a fluid recovery system to a support, such as a hospital bed side-rail or other support.

SUMMARY OF THE INVENTION

In one exemplary embodiment, this invention provides an apparatus for hanging a medical device. The apparatus includes a shaft, a mounting portion coupled to an end portion of the shaft and configured for mounting the apparatus for movement with respect to the medical device, and a hook portion positioned at an opposite end portion of the shaft and configured for hanging the apparatus from a support. The shaft is configured to permit rotation of the hook portion with respect to the mounting portion, thereby facilitating orientation of the hook portion with respect to the support.

In another exemplary embodiment, an assembly configured to be hung from a support is provided. The assembly includes a medical device and at least one hanger. Each hanger includes a shaft, a mounting portion coupled to an end portion of the shaft and coupled for movement with respect to the medical device, and a hook portion positioned at an opposite end portion of the shaft and configured for hanging from the support. The shaft of the hanger is configured to permit rotation of the hook portion with respect to the mounting portion of the hanger, thereby facilitating orientation of the hook portion with respect to the support.

In yet another exemplary embodiment, an assembly configured to be hung from a support is provided. The assembly includes a medical device and a plurality of hangers. Each hanger includes a shaft, a mounting portion coupled to an end portion of the shaft and coupled for pivotal movement with respect to the medical device, and a hook portion positioned at an opposite end portion of the shaft and configured for hanging from the support. The hangers are pivotable with respect to the medical device, thereby facilitating deployment of the hangers with respect to the medical device to an extended position. Furthermore, the hangers are positioned adjacent one another in the extended position for hanging from a substantially common point on the support.

In another exemplary embodiment, an assembly configured to be hung from a support is provided. The assembly includes a medical device, a handle coupled to the medical device and configured for grasping the medical device, and at least one hanger. The hanger includes a shaft, a mounting portion coupled to an end portion of the shaft and coupled to the handle, and a hook portion positioned at an opposite end portion of the shaft and configured for hanging from the support. The hanger is pivotable with respect to the handle, thereby facilitating deployment and retraction of the hanger with respect to the handle.

In yet another exemplary embodiment, in an assembly of a medical device and a plurality of hangers, a method of hanging the medical device to a support is provided. At least a portion of a shaft of each hanger is rotated with respect to a mounting portion of each hanger, thereby orienting a hook portion of each hanger with respect to the support. The hook portions of the hangers are positioned adjacent one another. The hook portion of each hanger is engaged to a substantially common point on the support, thereby hanging the medical device.

In another exemplary embodiment, in an assembly of a medical device and a plurality of hangers, a method of hanging the medical device to a support is provided. A mounting portion of each hanger is pivoted with respect to the medical device, thereby deploying a hook portion of each hanger with respect to the medical device. The hook portions of the hangers are positioned adjacent one another. The hook portion of each hanger is engaged to a substantially common point on the support, thereby hanging the medical device.

In still another embodiment, the assembly includes a medical device and a handle configured for grasping the medical device, the handle defining at least one aperture. At least a portion of the hanger extends into the aperture in the handle.

DETAILED DESCRIPTION OF THE INVENTION

Figure 2:
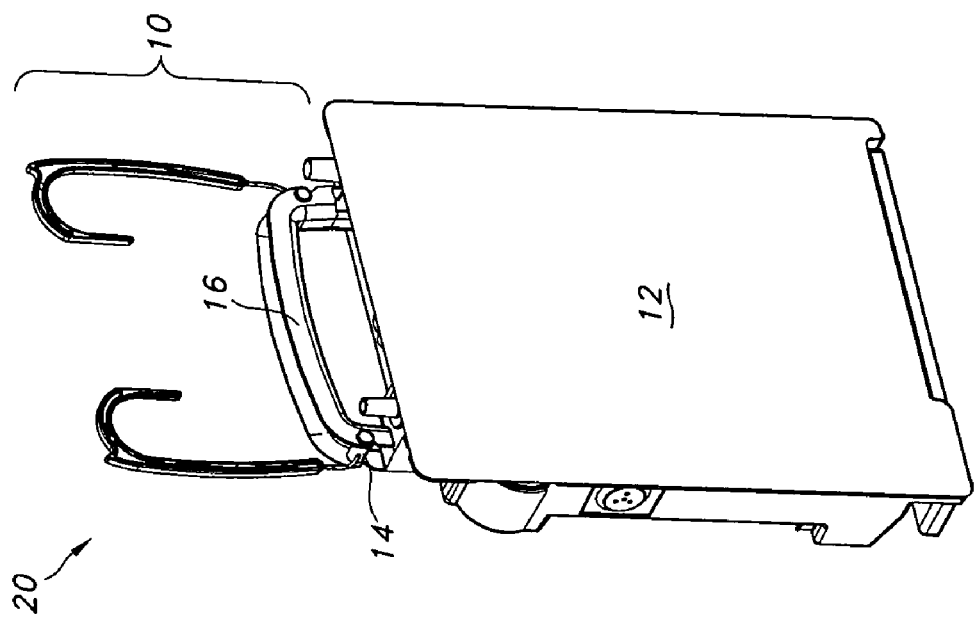
FIG. 2 is a perspective view of the assembly of FIG. 1, showing the hangers in a deployed position.

Although the invention is illustrated and described herein with reference to specific embodiments, the invention is not intended to be limited to the details shown. Rather, various modifications may be made in the details within the scope and range of equivalents of the claims and without departing from the invention.

Referring to the figures generally, in an exemplary embodiment an apparatus 10 for hanging a medical device 12 includes a shaft 22, a mounting portion 14 coupled to an end portion 24 of the shaft 22 and configured for mounting the apparatus 10 for movement with respect to the medical device 12, and a hook portion 28 positioned at an opposite end portion 26 of the shaft 22 and configured for hanging the apparatus 10 from a support 56A, 56B. The shaft 22 is configured to permit rotation of the hook portion 28 with respect to the mounting portion 14, thereby facilitating orientation of the hook portion 28 with respect to the support 56A, 56B.

In another exemplary embodiment, an assembly 20 configured to be hung from a support 56A, 56B is provided. The assembly 20 includes a medical device 12 and at least one hanger 10. Each hanger 10 includes a shaft 22, a mounting portion 14 coupled to an end portion 24 of the shaft 22 and coupled for movement with respect to the medical device 12, and a hook portion 28 positioned at an opposite end portion 26 of the shaft 22 and configured for hanging from the support 56A, 56B. The shaft 22 of the hanger 10 is configured to permit rotation of the hook portion 28 with respect to the mounting portion 14 of the hanger 10, thereby facilitating orientation of the hook portion 28 with respect to the support 56A, 56B.

In yet another exemplary embodiment, an assembly 20 configured to be hung from a support 56A, 56B is provided. The assembly 20 includes a medical device 12 and a plurality of hangers 10. Each hanger 10 includes a shaft 22, a mounting portion 14 coupled to an end portion 24 of the shaft 22 and coupled for pivotal movement with respect to the medical device 12, and a hook portion 28 positioned at an opposite end portion 26 of the shaft 22 and configured for hanging from the support 56A, 56B. The hangers 10 are pivotable with respect to the medical device 12, thereby facilitating deployment of the hangers 10 with respect to the medical device 12 to an extended position. Furthermore, the hangers 10 are positioned adjacent one another in the extended position for hanging from a substantially common point on the support 56B.

In another exemplary embodiment, an assembly 20 configured to be hung from a support 56A, 56B is provided. The assembly 20 includes a medical device 12, a handle 16 coupled to the medical device 12 and configured for grasping the medical device 12, and at least one hanger 10. The hanger 10 includes a shaft 22, a mounting portion 14 coupled to an end portion 24 of the shaft 22 and coupled to the handle 16, and a hook portion 28 positioned at an opposite end portion 26 of the shaft 22 and configured for hanging from the support 56A, 56B. The hanger 10 is pivotable with respect to the handle 16, thereby facilitating deployment and retraction of the hanger with respect to the handle 16.

In yet another exemplary embodiment, in an assembly of a medical device 12 and a plurality of hangers 10, a method of hanging the medical device 12 to a support 56A, 56B is provided. At least a portion of a shaft 22 of each hanger 10 is rotated with respect to a mounting portion 14 of each hanger 10, thereby orienting a hook portion 28 of each hanger 10 with respect to the support 56A, 56B. The hook portions 28 of the hangers 10 are positioned adjacent one another. The hook portion 28 of each hanger 10 is engaged to a substantially common point on the support 56B, thereby hanging the medical device 12.

In another exemplary embodiment, in an assembly of a medical device 12 and a plurality of hangers 10, a method of hanging the medical device 12 to a support 56A, 56B is provided. A mounting portion 14 of each hanger 10 is pivoted with respect to the medical device 12, thereby deploying a hook portion 28 of each hanger 10 with respect to the medical device 12. The hook portions 28 of the hangers 10 are positioned adjacent one another. The hook portion 28 of each hanger 10 is engaged to a substantially common point on the support 56B, thereby hanging the medical device.

In still another embodiment, the assembly includes a medical device 12 having a handle 16 configured for grasping the medical device 12, the handle 16 defining at least one aperture such as slot 52. At least a portion of the hanger 10 extends into the aperture 52 in the handle 16.

Figure 1:
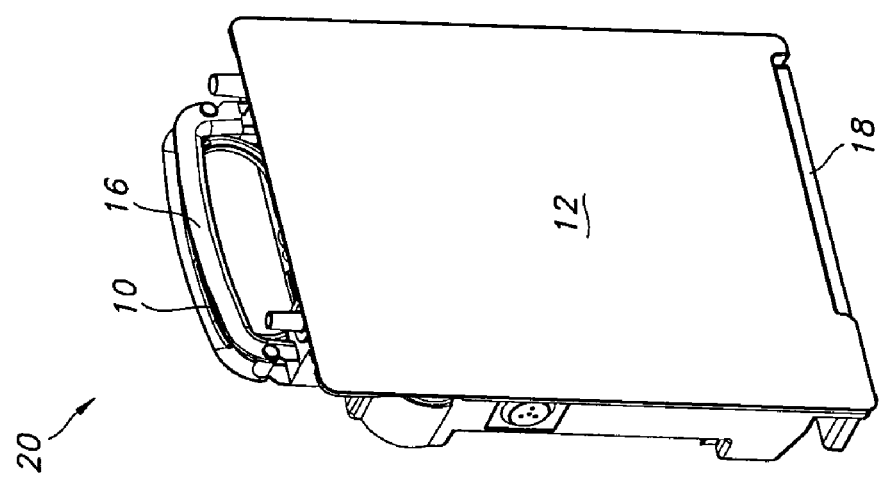
FIG. 1 is a perspective view of an exemplary embodiment of an assembly illustrating a medical device and a handle, shown with hanger components in a retracted position according to aspects of this invention.
Figure 5:
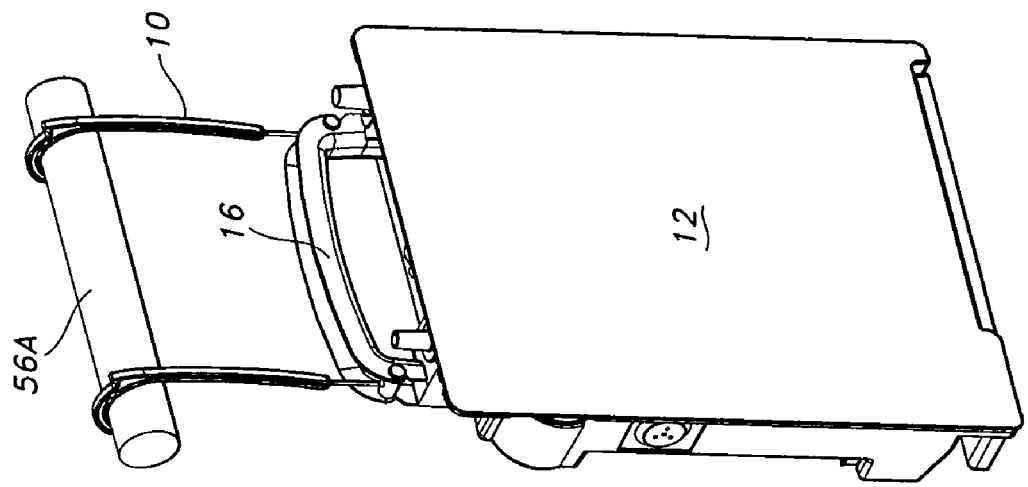
FIG. 5 is a perspective view the assembly of FIG. 2 shown with the hangers deployed and hanging from a cylindrical support according to aspects of this invention.
Figure 6:
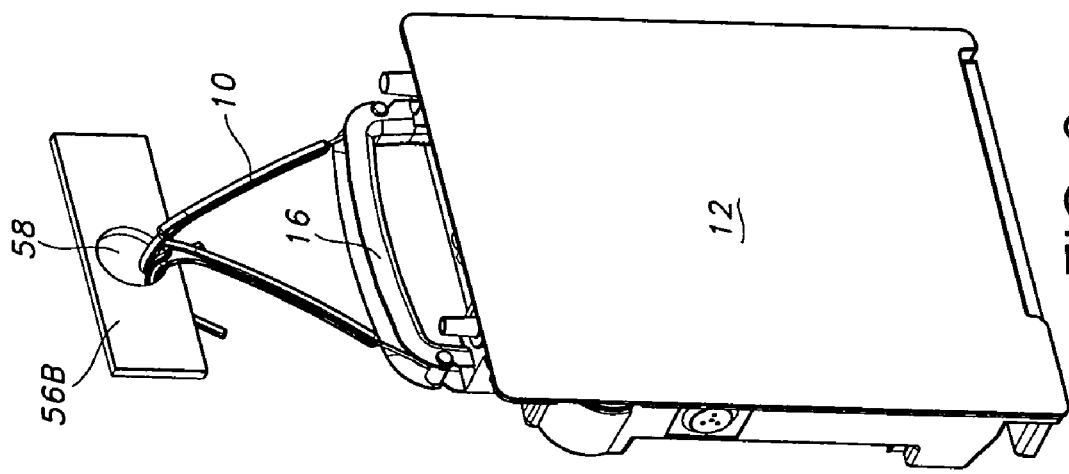
FIG. 6 is a perspective view the assembly of FIG. 2 shown with the hangers deployed and hanging from an aperture within a support according to aspects of this invention.

Referring now to FIGS. 1 and 2, an assembly embodying exemplary aspects of this invention is generally designated by the numeral "20." The assembly 20 is configured to be hung from a support 56A, 56B (as illustrated in FIGS. 5 and 6). The assembly 20 includes a medical device 12, a handle 16 attached to the medical device 12, hangers 10, and a swiveling base 18. The medical device 12 can be any medical device. For example, the medical device 12 can be a fluid recovery system such as a thoracic chest drainage system. The swiveling base 18 (shown in a retracted position) can be rotated to an extended position to provide a pedestal for the assembly 20. Though not shown, the assembly 20 also includes hoses for the introduction of matter from the pleural cavity of a patient and for the drawing of a vacuum.

Each hanger includes a mounting portion 14 for attachment to the handle 16. FIG. 1 shows the hangers 10 in a retracted or stowed position, while FIG. 2 shows the hangers 10 in a deployed or extended position. Ornamental features of the handle 16 are illustrated in co-pending Design Patent Application No. 29/192,612, now U.S. Pat. No. D517,897, which is incorporated herein by reference. The handle 16 can have a wide variety of ornamental shapes and configurations, including a variety of proportions, thicknesses, cross-sections, and curvatures. For example, ornamentation is provided by the arc-shaped profile of the handle 16, the "U" shaped cross-section of the handle 16, and the proportional size of the handle 16 with respect to the width and height of the medical device 12, among others.

FIGS. 3A-3D illustrate the hanger 10 in greater detail. Each hanger 10 includes a shaft 22, a mounting portion 14 coupled to an end portion 24 of the shaft 22, and a hook portion 28 positioned at an opposite end portion 26 of the shaft 22. A finger tab 30 is positioned to facilitate manipulation of the hook portion 28 with respect to the medical device 12. The finger tab 30 provides a surface by which a user of the medical device 12 can engage the hanger 10 to move the hanger 10 from its retracted position (FIG. 1) to its extended position (FIG. 2).

The hanger 10 is optionally molded such that the shaft 22, the mounting portion 14, and the hook portion 28 are integrally formed with respect to one another. Alternatively, the hanger 10 can be formed from an assembly of two or more components of the same or different materials. If molded, hanger 10 is optionally formed from plastic. Alternatively, hanger 10 can be formed from metallic or other materials using any known manufacturing technology.

The hanger 10 is in its relaxed position when the hook portion 28 resides in a plane of axis "B" of the mounting portion 14, as illustrated in FIGS. 3A-3D. The cross-sectional shape of the hook portion 28 includes a flanged perimeter 32 and a thinner central region 34. The flanged perimeter 32 adds structural strength to the hook portion 28 to help ensure that the hook portion 28 will retain its shape when hung from a support. The cross-sectional shape of the hook portion 28 is not limited to such a configuration, however. For example, the perimeter 32 may be thinner than the central region 34. Alternatively, the thickness of the hook portion 28 may be constant.

The mounting portion 14 is generally cylindrical in shape, oriented is along a central axis "B." The mounting portion 14 includes a central portion 40 and end portions 36. Circumferential recesses 38 are defined on the mounting portion 14 for engagement with the handle 16 attached to the medical device 12. The mounting portion 14 is not limited to such a configuration, however. For example, the central portion 40 may be a separate sleeve component that rotates around a pin, wherein the pin includes end portions 36. Gaps between the sleeve and the end portions 36 would act as circumferential recesses 38 for engagement with the handle 16.

The shaft 22 is flexible and generally cylindrical in shape, oriented along a central axis "A," substantially perpendicular to the axis "B" of the mounting portion 14. The shaft 22 is directly or indirectly coupled to the mounting portion 14.

The shaft 22 is optionally located such that the mounting portion 14 is positioned at an end portion 24 of the shaft 22. Alternatively, the end portion 24 of the shaft 22 is optionally spaced from the mounting portion 14.

The shaft 22 has a cross-sectional area smaller than that of the hook portion 28, and is sized to twist or deform or bend sufficiently for rotation of the hook portion 28 between the plane of axis "B" of the mounting portion 14 (the relaxed position of the hanger 10 shown in FIGS. 3A-3B) and a plane substantially perpendicular to axis "B" of the mounting portion 14 (the non-relaxed position of the hanger 10 shown in FIGS. 5 and 6).

The shape of the shaft 22 is not limited to a cylindrical shape or a round cross-sectional shape. For example, the cross-sectional shape may be square, triangular, or any other shape capable of twisting or otherwise deforming. Also, rotation of shaft 22 can be accomplished by forming shaft 22 or hanger 10 from multiple components coupled to one another in such a way to achieve rotation of the hook portion 28 with respect to the mounting portion 14. For example, the hanger 10 is optionally formed from telescoping components, rotationally coupled components, or components joined for pivotal or rotational movement with respect to one another.

As stated previously herein, the hanger 10 is optionally molded from plastic. For example, the hanger 10 can be formed using an injection molding process. However, the hanger may be molded or otherwise formed from a variety of materials, so long as the hook portion 28 is sufficiently rigid to hang from a support 56A, 56B, and the shaft 22 is sufficiently flexible to twist or otherwise deform or rotate for rotation of the hook portion 28 with respect to the mounting portion 14. For example, the hanger 10 may be molded from rubber, or formed from composite material.

FIGS. 4A-4D illustrate the handle 16 in greater detail. As mentioned previously herein, ornamental features of the handle 16 are illustrated in co-pending Design Patent Application No. 29/192,612, now U.S. Pat. No. D517,897. The handle 16 includes a grasping portion 42 and an elongated groove 54. The grasping portion 42 is provided with an ornamental curvature, and the elongated groove 54 is provided with an ornamental "U", shaped cross-section. These ornamental features can be modified to provide a different ornamental appearance, depending upon design preferences, without impact on the use or operation of the handle 16.

Notches 44 are defined in the handle 16 for engagement with the mounting portion 14 of each hanger 10. More specifically, each circumferential recess 38 defined on a mounting portion 14 of a hanger 10 engages a notch 44 defined in the handle 16. The central portion 40 of the mounting portion 14 is positioned within the ornamental elongated groove 54 between opposed walls of the handle 16, and the end portions 36 are positioned on an outside surface of the grasping portion 42, as illustrated in FIGS. 1, 2, 5, and 6.

Figure 3A:
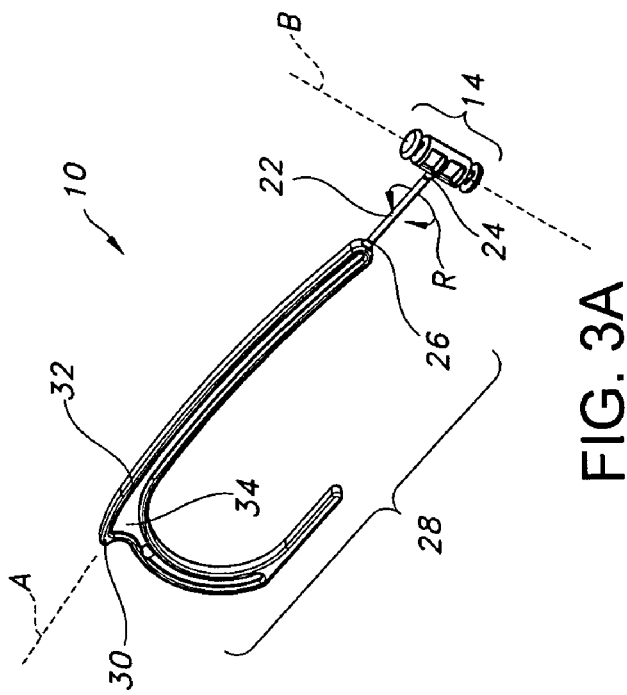
FIG. 3A is a detailed perspective view of a hanger of FIG. 1 according to aspects of this invention.
Figure 3D:
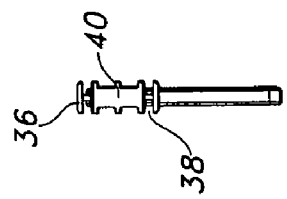
FIG. 3D is a right side view of the hanger of FIG. 3A.
Figure 3C:
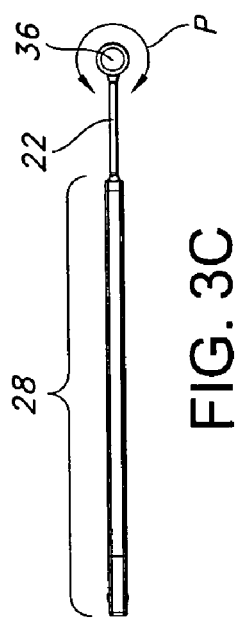
FIG. 3C is a top view of the hanger of FIG. 3A.
Figure 3B:
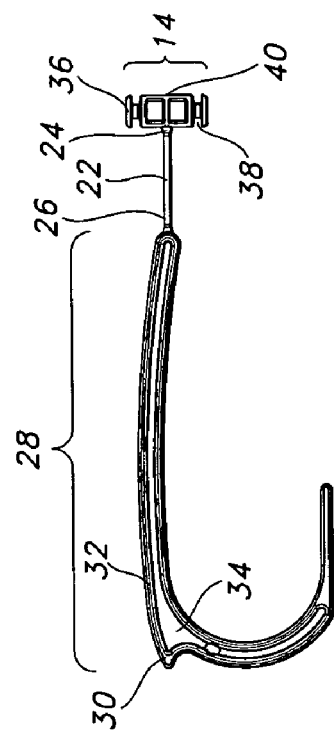
FIG. 3B is a front view of the hanger of FIG. 3A.

The orientation of the central portion 40 combined with end portions 36 prevents axial movement of mounting portion 14 along the "B" axis (represented in FIG. 3A). The circumferential recesses 38 are engaged within the notches 44, thereby facilitating pivotal movement "P" (represented in FIG. 3C).

Figure 4B:
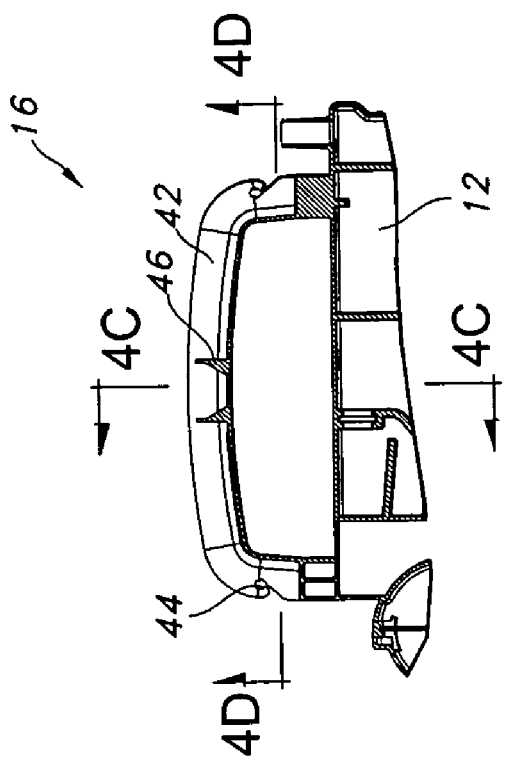
FIG. 4B is a front cross-sectional view of the handle of the assembly of FIG. 4A.
Figure 4D:
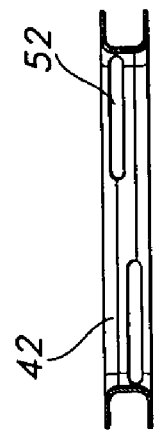
FIG. 4D is a bottom cross-sectional view of the handle of the assembly of FIG. 4B.
Figure 4A:
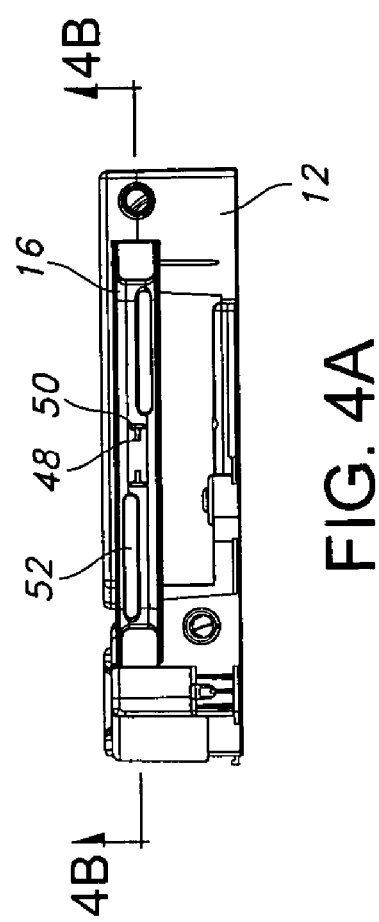
FIG. 4A is a plan view of the assembly of FIG. 1 shown without the hangers according to aspects of this invention.

As illustrated in FIGS. 4A and 4D, slots 52 are defined within the handle 16. More specifically, the slots 52 are defined along a bottom surface of the ornamental elongated groove 54 of the ornamental grasping portion 42. Such slots 52 are configured to accommodate at least a portion of each hook portion 28 when the hangers 10 are in their retracted or stowed positions (illustrated in FIG. 1). When in this stowed position, the hook portions 28 of hangers 10 are substantially protected so as to reduce the unintended hooking of hook portions 28 on objects adjacent to the medical device 12, such as sheets, tubes, wires and other objects found in the health care environment.

It will be understood that such unintended hooking can be frustrating during use or set up of the medical device 12. Medical devices such as the thoracic chest drain shown in the figures often need to be set up quickly and easily. By reducing the accessibility of hook portions 28 of hangers 10 when in the stowed position, the frustration associated with unintended hooking is reduced or eliminated.

Figure 4C:
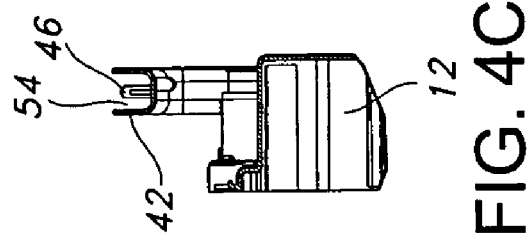
FIG. 4C is a right side cross-sectional view of the assembly of FIG. 4B.

FIGS. 4A-4C illustrate protrusions 46 extending from the handle 16. Each protrusion 46 includes a flat projection 50 and a rib 48 provided to support the flat projection 50. The protrusions 46 separate the hangers 10 from one another when the hangers 10 are in the retracted position shown in FIG. 1. The protrusions 46 also help to guide the hook portions 28 of hangers 10 into respective slots 52 as the hangers 10 are moved from their extended position (FIG. 2) to their retracted position (FIG. 1). This feature is helpful during the assembly of the medical device 12 for shipment and during the use of the medical device 12.

The hangers 10 may initially be in their retracted position within the handle 16 as illustrated in FIG. 1. The protrusions 46 ensure the hangers 10 are properly aligned within the ornamental elongated groove 54 of the ornamental grasping portion 42 of the handle 16. The slots 52 defined along a bottom surface of the ornamental elongated groove 54 accommodate at least a portion of each hook portion 28, thereby permitting the hook portions 28 to lay flush within the grasping portion 42. In other words, the hangers 10 in their retracted position do not substantially change the shape of the handle 16, and do not interfere with a user's ability to hold the grasping portion 42 to move the medical device 12 as desired. The hangers 10 are virtually hidden when in their retracted position.

In use, a user may pull up on each finger tab 30, pivoting each hanger 10 to the deployed position illustrated in FIG. 2. It is the orientation of the circumferential recesses 38 of the mounting portions 14 with respect to the handle 16 that facilitates the pivotal movement of the hangers 10 with respect to the handle 16. In other words, the pivotal movement "P" of each mounting portion 14 (represented in FIG. 3C) facilitates deployment or retraction (at this point, deployment) of each respective hanger 10 with respect to the handle 16.

In the deployed position illustrated in FIG. 2, each hanger 10 is oriented in a plane substantially perpendicular to axis "B" of each respective mounting portion 14 (the non-relaxed position of the hanger 10). As described previously herein, each shaft 22 is flexible and generally cylindrical in shape, oriented along a central axis "A," substantially perpendicular to the axis "B" of each respective mounting portion 14. Each shaft 22 is sized to twist sufficiently for rotation of the hook portion 28 with respect to the mounting portion 14.

At this point in the use of this assembly 20, the user rotates each hook portion 28 from a plane substantially perpendicular to axis "B" of each respective mounting portion 14 (the non-relaxed position of the hanger 10) to a plane substantially parallel to axis "B" (the relaxed position of the hanger 10). More specifically, the hanger 10 is returned to its relaxed position, as illustrated in FIGS. 3A-3D. The rotational movement, as represented by "R" in FIG. 3A, rotates the hook portions 28 from the position illustrated in FIG. 2 to the position illustrated in FIG. 5. Such rotational movement "R" of the shaft 22 facilitates the orientation of the hook portion 28 with respect to a support 56A, 56B. The user may then engage the hook portions 28 of the hangers 10 to a support 56A, 56B, thereby hanging the medical device 12.

FIG. 5 illustrates a cylindrical support 56A, while FIG. 6 illustrates a support 56B with an aperture 58 from which the medical device 12 hangs. The shape of the support may vary. For example, the support may have a square cross-section, a rectangular cross-section, a triangular cross-section, or any other cross-section conducive to engagement with the hook portions 28 of the hangers 10. Alternatively, the support may be a member that includes apertures or notches of various shapes and sizes, as long as these configurations are conducive to engagement with the hook portions 28 of the hangers 10.

Also, the support may be oriented in a wide variety of positions and directions. For example, the support can be oriented along an axis that is substantially parallel to the face of the medical device 12 (as shown in FIG. 5), substantially perpendicular to the face of the medical device 12, or at any other angle. The support can be a rod, tube, or other structure found in a medical or surgical environment. The support can also be a knob, furniture component, or any other structure proximal to a patient that is capable of supporting the medical device.

Alternatively, the support may define an aperture such as aperture 58 of support 56B through which one or more hook portions 28 can extend. The support may also define a recess or other configuration that provides a surface from which the medical device 12 can be hung.

The assembly illustrated in the figures is particularly well adapted for hanging a medical device from a wide variety of supports in a wide variety of configurations and orientations. Specifically, the hook portions 28 can be oriented in any number of planes. The hook portions 28 can also be faced in opposite directions to capture a support member. The hook portions 28 can also be positioned adjacent one another in a plane substantially parallel to the face of the medical device 12, in a plane substantially perpendicular to the face of the medical device 12, or in a variety of planes. When positioned adjacent one another as shown in FIG. 6, the hook portions 28 are configured to engage a substantially common point or location of a support (e.g., an aperture, a knob, etc.). The hook portions 28 can also be spaced from one another as shown in FIG. 5.

When removal of the medical device 12 from a support 56A, 56B is desired, the user may remove the hook portions 28 of the hangers 10 from the support 56A, 56B. At this point in the use of this assembly 20, the hangers 10 are oriented with respect to the handle 16 as illustrated in FIG. 5 (without the support 56A) in their relaxed positions, i.e., each hook portion 28 resides in a plane of axis "B" of its respective mounting portion 14.

The user may then rotate each hook portion 10 from a plane substantially parallel to axis "B" of each respective mounting portion 14 to a plane substantially perpendicular to axis "B." Each shaft 22 twists or otherwise moves sufficiently for rotation of the hook portions 28. In other words, the rotational movement, as represented by "R" in FIG. 3A, rotates the hook portions 10 from the position illustrated in FIG. 5 to the position illustrated in FIG. 2. Such rotational movement "R" of the shaft 22 facilitates the orientation of the hook portion 28 with respect to the handle 16.

The hangers 10 are then pivoted toward the handle 16. As explained previously herein, the pivotal movement "P" of each mounting portion 14 (represented in FIG. 3C) facilitates deployment or retraction (at this point, retraction) of each respective hanger 10 with respect to the medical device 12. As each hanger 10 is pivoted toward the grasping portion 42 of the handle 16, the flat projection 50 of each protrusion 46 (illustrated in FIGS. 4A-4C) guides each hook portion 28 for proper alignment with respect to one another. As explained previously herein, the protrusions 46 separate the hangers 10 from one another in their fully retracted (or stowed) positions.

As each hanger 10 is pivoted toward the grasping portion 42 of the handle 16, at least a portion of each hook portion 28 passes through the slots 52 defined within the grasping portion 42. As explained previously herein, the slots 52 are configured to accommodate at least a portion of each hook portion 28 when the hangers 10 are in their fully retracted positions, thereby permitting the hook portions 28 to lay substantially flush within the ornamental grasping portion 42 (as illustrated in FIG. 1). The user may then hold the grasping portion 42 to move the medical device 12 as desired.

While preferred embodiments of the invention have been shown and described herein, it will be understood that such embodiments are provided by way of example only. Numerous variations, changes, and substitutions will occur to those skilled in the art without departing from the spirit of the invention. For example, the hook portion 28 of the hanger 10 is not limited to a rounded hook shape as illustrated in FIGS. 1, 2, 3A, 3B, 5, and 6. Alternatively, the shape of hook portion 28 may include squared or angular interior corners.

Also, the hanger or hangers 10 can be mounted to the medical device 12 as opposed to being mounted to the handle 16. For example, the hangers 10 could alternatively be mounted to surfaces of the medical device 12 such as the side surfaces of the medical device 12. It has been discovered, however, that by mounting the hangers 10 to the handle 16 as opposed to the medical device 12, it is possible to avoid the provision of mounting structures on surfaces of the medical device 12. Also, the hangers 10 can be stowed in the handle 16 without altering the structure of the medical device 12. Additionally, mounting hangers 10 to the handle 16, as opposed to the sides of the medical device 12, avoids the increased width resulting from mounting structures extending from the sides of the medical device 12.

Accordingly, it is intended that the appended claims cover all such variations as fall within the spirit and scope of the invention.

What is claimed is:

1. An apparatus for hanging a medical device, said apparatus comprising:
   a shaft;
   a mounting portion coupled to an end portion of said shaft and configured for mounting said apparatus for movement with respect to the medical device between a retracted position and a deployed position, wherein said mounting portion extends along a longitudinal axis and said longitudinal axis of said mounting portion is oriented perpendicular to an axis of said shaft, and wherein said mounting portion defines at least one circumferential recess positioned on an exterior cylindrical surface of said mounting portion to facilitate the movement of said apparatus with respect to the medical device; and
   a hook portion positioned at an opposite end portion of said shaft and configured for hanging said apparatus from a support when said apparatus is in said deployed position, wherein said hook portion is positionable in a plane parallel to the longitudinal axis of said mounting portion;
   wherein said shaft is configured to permit rotation of said hook portion with respect to said mounting portion, thereby facilitating orientation of said hook portion with respect to the support.

2. The apparatus of claim 1, wherein at least one of said shaft, said mounting portion, and said hook portion is molded.

3. The apparatus of claim 1, wherein said shaft is generally cylindrical in shape.

4. The apparatus of claim 1, wherein said shaft has a cross-sectional area smaller than that of said hook portion.

5. The apparatus of claim 1, wherein said shaft is flexible.

6. The apparatus of claim 1, wherein said shaft is sized to twist sufficiently for rotation of said hook portion between said plane of said axis of said mounting portion and a plane substantially perpendicular to said axis of said mounting portion.

7. The apparatus of claim 1, wherein the medical device is a fluid recovery system.

8. The apparatus of claim 7, wherein the medical device is a thoracic cavity drainage system.

9. The apparatus of claim 1, wherein said mounting portion is spaced from an end portion of said shaft.

10. An assembly configured to be hung from a support, said assembly comprising:
    a thoracic cavity drainage system including a collection chamber for storing fluid and a handle for grasping by a user; and
    at least one hanger coupled to said handle comprising
    an elongated shaft;
    a mounting portion coupled to an end portion of said elongated shaft and coupled for pivotal movement with respect to said drainage system about a longitudinal axis of said mounting portion; and
    a hook portion positioned at an opposite end portion of said elongated shaft and configured for hanging from the support;
    wherein said elongated shaft of said hanger is configured to permit rotation of said hook portion with respect to said mounting portion of said hanger about a longitudinal axis of the elongated shaft, thereby facilitating orientation of said hook portion with respect to the support, and
    wherein a slot is defined in said handle to accommodate at least a portion of said hook portion when said hanger is in a retracted position.

11. The assembly of claim 10 wherein said handle is integral to said drainage system.

12. The assembly of claim 11, wherein said mounting portion pivots with respect to said handle, thereby facilitating deployment or retraction of said hanger with respect to said handle.

13. The assembly of claim 10, wherein said hanger is stowed in said retracted position, thereby preventing unintentional hooking of said hook portion.

14. The assembly of claim 10, wherein said assembly further comprises a plurality of hangers.

15. An assembly configured to be hung from a support, said assembly comprising:
    a medical device; and
    a plurality of hangers, each comprising
    a shaft;
    a mounting portion coupled to an end portion of said shaft and coupled for pivotal movement with respect to said medical device;
    a hook portion positioned at an opposite end portion of said shaft and configured for hanging from the support;
    wherein said shaft of each hanger is configured to permit rotation of said hook portion with respect to said mounting portion, thereby facilitating orientation of said hook portion of each hanger with respect to the support for positioning the medical device; and
    wherein said hangers are pivotable with respect to said medical device, thereby facilitating deployment of said hangers with respect to said medical device to an extended position, and a surface of the medical device is positioned to contact said hook portions of said hangers in a retracted position of the hangers, thereby limiting movement of the hook portions of the hangers in the retracted position; and
    wherein said hangers are positioned adjacent one another in said extended position for hanging from a substantially common point on said support.

16. The assembly of claim 15, further comprising a handle coupled to said medical device.

17. The assembly of claim 16, wherein said mounting portion pivots with respect to said handle.

18. An assembly configured to be hung from a support, said assembly comprising:
    a thoracic cavity drainage system defining a collection chamber for storing fluid;
    a handle coupled to said drainage system and configured for grasping said drainage system; and
    at least one hanger comprising a flexible shaft;
    a mounting portion having a longitudinal axis, said mounting portion being coupled to an end portion of said flexible shaft and coupled to said handle for pivotal movement only about said longitudinal axis; and
    a hook portion positioned at an opposite end portion of said flexible shaft and configured for hanging from the support;

wherein said hanger is pivotable with respect to said handle, thereby facilitating deployment and retraction of said hanger with respect to said handle, wherein said flexible shaft is configured to twist sufficiently to permit rotation of said hook portion with respect to said mounting portion about a longitudinal axis of said flexible shaft, thereby facilitating orientation of said hook portion of said hanger with respect to the support for positioning the drainage system.

19. An assembly configured to be hung from a support, said assembly comprising:

a thoracic cavity drainage system;

a handle coupled to said drainage system and configured for grasping said drainage system, said handle defining at least one aperture; and at least one hanger comprising a shaft;

a mounting portion coupled to an end portion of said shaft and coupled to said handle; and a hook portion positioned at an opposite end portion of said shaft and configured for hanging from the support;

wherein said hanger is pivotable with respect to said handle, thereby facilitating deployment and retraction of said hanger with respect to said handle; and wherein at least a portion of said hook portion of said hanger extends into said aperture in said handle when said hanger is in a retracted position.

* * * * *